(12) United States Patent
Day-Lollini et al.

(10) Patent No.: US 7,476,676 B2
(45) Date of Patent: Jan. 13, 2009

(54) METHODS FOR INCREASING BONE FORMATION USING INHIBITORS OF GLYCOGEN SYNTHASE KINASE-3β

(75) Inventors: Patricia Ann Day-Lollini, San Carlos, CA (US); Leyi Gong, San Mateo, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 945 days.

(21) Appl. No.: 10/339,193

(22) Filed: Jan. 9, 2003

(65) Prior Publication Data

US 2003/0176484 A1    Sep. 18, 2003

Related U.S. Application Data

(60) Provisional application No. 60/348,055, filed on Jan. 10, 2002.

(51) Int. Cl.
*C07D 471/04* (2006.01)
*A01N 43/42* (2006.01)
*A01N 43/38* (2006.01)

(52) U.S. Cl. .................. 514/257; 514/285; 514/415

(58) Field of Classification Search ............... 514/414, 514/235.8, 257, 285, 415
See application file for complete search history.

(56) References Cited

U.S. PATENT DOCUMENTS 6,417,185 B1 * 7/2002 Goff et al. ............... 514/235.8

6,479,490 B2 * 11/2002 Gong et al. ............... 514/235.5

FOREIGN PATENT DOCUMENTS

| WO | WO 99/65897 A1 | 12/1999 |
| WO | WO00/38675 | * 7/2000 |
| WO | WO 01/56993 A2 | 8/2001 |
| WO | WO 02/066461 A1 | 8/2002 |
| WO | WO 02/068415 A1 | 9/2002 |

OTHER PUBLICATIONS

Coghlan et al., Selective Small Molecule Inhibitors of Glycogen Synthase Kinase-3 Modulate Glycogen Metabolism and Gene Transcription, Chemistry and Biology, 2000, vol. 7, pp. 793-803.*
Hochberg, et al., Changes in Bone Density and Turnover Explain the Reductions in Incidence of Nonvertebral Fractures That Occur During Treatment with Antiresorptive Agents, Journal of Clinical Endocrinology and Metabolism, 2002, vol. 87, pp. 1586-1592.*
Coghlan et al. (Selective Small Molecule Inhibitors of Glycogen Synthase Kinase-3 Modulate Glycogen Metabolism and Gene Transcription, Chemistry and Biology, 2000, vol. 7, pp. 793-803).*
Hochberg, et al. (Changes in Bone Density and Turnover Explain the Reductions in Incidence of Nonvertebral Fractures That Occur During Treatment with Antiresorptive Agents, Journal of Clinical Endocrinology and Metabolism, 2002, vol. 87, issue 4, pp. 1586-1592).*
Nordenstrom et al. (Biochemical Hyperthyroidism and Bone Mineral Status in Patients Treated Long-Term With Lithium, Metabolism, 1994, vol. 43, No. 12, pp. 1563-1567).*
Wang, J. et. al., "Igf1 Promotes Longitudinal Bone Growth by Insulin-like Actions Augmenting Chrondrocyte Hypertrophy," *FASED Journal*, 1999, vol. 13 (14) pp. 1985-1990.

* cited by examiner

*Primary Examiner*—Sreeni Padmanabhan
*Assistant Examiner*—Kara R McMillian
(74) *Attorney, Agent, or Firm*—Grant D. Green

(57) ABSTRACT

This invention relates to the use of inhibitors of glycogen synthase kinase-3β to increase bone formation.

11 Claims, No Drawings

METHODS FOR INCREASING BONE FORMATION USING INHIBITORS OF GLYCOGEN SYNTHASE KINASE-3β

CROSS-REFERENCE TO RELATED APPLICATIONS

This application claims the priority benefit under Title 35 U.S.C. 119(e) of U.S. Provisional Application No. 60/348,055, filed Jan. 10, 2002, the disclosure of which is herein incorporated by reference.

BACKGROUND OF THE INVENTION

1. Field of the Invention

The present invention is directed to the use of inhibitors of glycogen synthase kinase-3β (GSK-3β) to promote bone formation and treat bone metabolic diseases such as osteoporosis.

2. State of the Art

Glycogen synthase kinase (GSK) is a serine/threonine kinase for which two isoforms, α and β, have been identified. Glycogen synthase kinase-3β (GSK-3β) was originally identified as a protein kinase which phosphorylated and inactivated glycogen synthase, a key enzyme regulating insulin-stimulated glycogen synthesis ((see Embi et al., *Eur. J. Biochem.* 107, 519-527, (1980); Rylatt et al., *Eur. J. Biochem.* 107, 529-537, (1980); and Vandenheede et al., *J. Biol. Chem.* 255, 11768-11774, (1980)). Subsequently, it was discovered that GSK-3β is inhibited upon insulin activation thereby allowing the activation of glycogen synthase. Therefore, inhibition of GSK-3β stimulates insulin-dependent processes and is useful in the treatment of type 2 diabetes which is characterized by decreased sensitivity to insulin and an increase in blood glucose level. A number of drugs such as 5-iodotubercidin®, metformin®, troglitazonem®, have been used to treat diabetes. These drugs however have limited application because metformin® can cause hypoglycemia, troglitazonem® can cause severe hepatoxicity and 5-iodotubercidin®, a known GSK-3 inhibitor, inhibits other serine/threonine and tyrosine kinases.

Recently, it has been discovered that GSK-3β plays a role in pathogenesis of Alzheimer's disease ((see Lovestone et al., *Current Biology*, 4, 1077-86 (1994), Brownlees et al., *Neuroreport*, 8, 3251-3255 (1997), Takashima et al., *PNAS* 95, 9637-9641 (1998), and Pei et al., *J Neuropathol. Exp.*, 56, 70-78 (1997)) and bipolar disorder (see Chen et al., *J. Neurochemistry*, 72, 1327-1330 (1999)). It has also been discovered that GSK-3β is involved in blocking of early immune response gene activation via NF-AT and regulation of apoptosis (see Beals et al., *Science*, 275, 1930-33 (1997) and Pap, M. et al. *J. Biochem.* 273, 19929-19932, (1998)). Additionally, GSK-3β is reported to be required for the NF-κB mediated survival response in the TNF-α signalling pathway involved in the proinflammatory response to infection ((Hoeflich et.al., *Nature*, 406, 86-90 (2000)).

Furthermore, GSK-3β is also known to regulate the degradation of a protein (β-catenin) which controls the activity of TCF family of transcription factors ((see., Dale, T. C., *Biochem. J.* 329, 209-223 (1998); Clevers, H. & van de Wetering, M., *Trends in Genetics* 13, 485-489 (1997); Staal, F. J. T. et al., *International Immunology* 11, 317-323 (1999)). The pathway has been shown to regulate the transformation of colonic epithelial cells.

GSK-3β inhibitors are described in the following references: WO99/65897 (U.S. Pat. No. 6,417,185 (Chiron)), WO 01/20727A1 (U.S. Pat. No. 6,361,346 (Sanofi-Synthelabo)), EP 1 136 493 A1(Sanofi-Synthelabo), EP 1 136 489 A1(Sanofi-Synthelabo), EP 1 136 486 A1 (Sanofi-Synthelabo), EP 1 136 483 A1(Sanofi-Synthelabo), EP 1 136 099A1(Sanofi-Synthelabo), ) WO 2000/021927 (SKB), WO 2001/049709, WO 2001/056567 (US 2001039275 (Novo Nordisk)), WO 2001/081345, WO 2001/085685, WO 2001/009106 (SKB) and WO2001/52862 (U.S. Pat. No. 6,323,029 (Isis)), WO2001/37819, WO2001/60374, EP 1 106 180A1 (CNRS), WO2000/38675 (SKB), WO 2002096905 (Vertex), WO 2002088078 (Vertex), WO 2002085909, US 2002156087, US 2002147146, WO 2002079197, WO 2002066480, WO 2002065979, WO 2002062795, WO 2002062789, WO 2002059112, WO 2002050079, WO 2002050073, WO 2002050066, WO 2002032896, WO 2002024694, WO 2002022604, WO 2002020495, WO 2002018346, EP 1184385, EP 1184384, EP 1184383 and WO 2001085685.

SUMMARY OF THE INVENTION

The present invention is directed to the use of inhibitors of glycogen synthase kinase-3β (GSK-3β) to promote bone formation.

In one aspect, the invention is directed to the use of GSK-3β inhibitors to increase bone mineral density in a patient. In another aspect, the invention is directed to the use of GSK-3β inhibitors to reduce the rate of fracture and/or increase the rate of fracture healing in a patient. In another aspect, the invention is directed to the use of GSK-3β inhibitors to increase cancellous bone formation and/or new bone formation in a patient. In another aspect, the invention is directed to the use of GSK-3β inhibitors to treat osteoporosis. Accordingly, in one aspect, this invention is directed to the use of 3-indolyl-4-phenyl-1H-pyrrole-2,5-dione derivatives represented by Formula (I) to increase bone formation in a mammal:

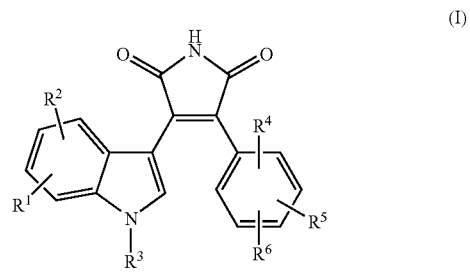

(I)

wherein:

$R^1$ and $R^2$ independently represent hydrogen, alkyl, halo, haloalkyl, alkylthio, hydroxy, alkoxy, cyano, nitro, amino, acylamino, monoalkylamino, or dialkylamino;

$R^3$ represents hydrogen, alkyl, cycloalkyl, heteroalkyl, —COR$^7$ (wherein R$^7$ is hydrogen or alkyl), or phenyl optionally substituted with one or two substituents independently selected from the group consisting of hydrogen, alkyl, haloalkyl, alkylthio, hydroxy, alkoxy, cyano, nitro, amino, acylamino, monoalkylamino, and dialkylamino;

$R^4$ and $R^5$ independently represent hydrogen, alkyl, halo, haloalkyl, alkylthio, hydroxy, alkoxy, cyano, nitro, amino, acylamino, monoalkylamino, or dialkylamino;

$R^6$ is heteroalkyl, heterocyclyl, heterocyclylalkyl, heteroalkylsubstituted heterocyclyl, heteroalkylsubstituted cycloalkyl, hetereosubstituted cycloalkyl, —OR$^8$, —S(O)$_n$R$^8$ (wherein n is 0 to 2; and R$^8$ is heteroalkyl, heteroaralkyl, heterocyclyl, or heterocyclylalkyl), —NR$^9$R$^{10}$ (wherein R$^9$ is hydrogen or alkyl and $R^{10}$ is heteroalkyl, heteroaralkyl, heterosubstituted cycloalkyl, heterocyclyl, or heterocyclylalkyl), or -X-(alkylene)-Y-Z (wherein X is a covalent bond, —O—, —NH—, or —S(O)$_{n1}$— where n1 is 0 to 2, and Y is —O—, —NH—, or —S—, and Z is heteroalkyl or $SiR^{11}R^{12}R^{13}$ where $R^{11}$, $R^{12}$ and $R^{13}$ are independently hydrogen or alkyl), or $R^6$ together with $R^4$ forms a methylenedioxy or ethylenedioxy group when they are adjacent to each other; or a pharmaceutically acceptable salt thereof.

In another aspect, the invention is directed to the use of GSK-3β inhibitors to increase bone formation where the inhibitor is selected from the compounds disclosed in WO99/65897 (Chiron), WO 01/20727A1 (Sanofi-Synthelabo), EP 1 136 493 A1(Sanofi-Synthelabo), EP 1 136 489 A1(Sanofi-Synthelabo), EP 1 136 486 A1 (Sanofi-Synthelabo), EP 1 136 483 A1(Sanofi-Synthelabo), EP 1 136 099A1 (Sanofi-Synthelabo), ) WO 2000/021927 (SKB), WO 2001/049709, WO 2001/056567 (Novo Nordisk), WO 2001/081345, WO 2001/085685, WO 2001/009106 (SKB) and WO2001/52862 (Isis), WO2001/37819, WO2001/60374, EP 1 106 180A1 (CNRS), WO2000/38675 (SKB).

WO 01/20727A1 (Sanofi-Synthelabo), EP 1 136 493 A1(Sanofi-Synthelabo), EP 1 136 489 A1(Sanofi-Synthelabo), EP 1 136 486 A1 (Sanofi-Synthelabo), EP 1 136 483 A1(Sanofi-Synthelabo), EP 1 136 099A1 (Sanofi-Synthelabo) disclose various pyrimidine-4(1H)-one derivatives WO2001/37819 discloses indirubine derivatives. WO2001/60374 discloses paullone derivatives. EP 1 106 180A1 discloses hymenialdisine derivatives.

DETAILED DESCRIPTION OF THE INVENTION

Definitions

The following terms used with respect to the description of compounds of Formula (I) in the specification and claims have the meanings given below.

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, n-butyl, iso-butyl, tert-butyl, pentyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkoxy" means a radical —OR where R is an alkyl as defined above e.g., methoxy, ethoxy, propoxy, butoxy and the like.

"Alkylthio" means a radical —SR where R is an alkyl as defined above e.g., methylthio, ethylthio, propylthio, butylthio, and the like.

"Acyl" means a radical —C(O)R, where R is hydrogen, alkyl, cycloalkyl, cycloalkylalkyl, phenyl or phenylalkyl wherein alkyl, cycloalkyl, cycloalkylalkyl, and phenylalkyl are as defined herein. Representative examples include, but are not limited to formyl, acetyl, cylcohexylcarbonyl, cyclohexylmethylcarbonyl, benzoyl, benzylcarbonyl, and the like.

"Acylamino" means a radical —NR'C(O)R, where R' is hydrogen or alkyl, and R is hydrogen, alkyl, cycloalkyl, cycloalkylalkyl, phenyl or phenylalkyl wherein alkyl, cycloalkyl, cycloalkylalkyl, and phenylalkyl are as defined herein. Representative examples include, but are not limited to formylamino, acetylamino, cylcohexylcarbonylamino, cyclohexylmethyl-carbonylamino, benzoylamino, benzylcarbonylamino, and the like.

"Cycloalkyl" refers to a saturated monovalent cyclic hydrocarbon radical of three to seven ring carbons e.g., cyclopropyl, cyclobutyl, cyclohexyl, 4-methylcyclohexyl, and the like.

"Cycloalkylalkyl" means a radical —$R^aR^b$ where $R^a$ is an alkylene group and $R^b$ is cycloalkyl group as defined herein, e.g., cyclohexylmethyl, and the like.

"Dialkylamino" means a radical —NRR' where R and R' independently represent an alkyl, cycloalkyl, or cycloalkylalkyl group as defined herein. Representative examples include, but are not limited to dimethylamino, methylethylamino, di(1-methylethyl)amino, (cyclohexyl)(methyl)amino, (cyclohexyl)(ethyl)amino, (cyclohexyl)(propyl)amino, (cyclohexylmethyl)(methyl)amino, (cyclohexylmethyl)(ethyl)amino, and the like.

"GSK-3β inhibitor" or "inhibitor of GSK-3β" means a compound that has an IC50 against GSK-3β of less than_100 nM, preferably less than 50 nM, most preferably less than 10 nM when measured by the in vitro GSK-3β assay described in Biological Example 1 herein. Preferably, the GSK-3β inhibitor is an organic molecule of molecular weight less than 1000 daltons. Particularly useful are GSK-3β inhibitors that show selectivity for GSK-3β over other kinases, such as for example, PKC, cdk1, cdk2, cdk4 and c-SRC.

"Halo" means fluoro, chloro, bromo, or iodo, preferably fluoro and chloro.

"Haloalkyl" means alkyl substituted with one or more same or different halo atoms, e.g., —$CH_2Cl$, —$CF_3$, —$CH_2CF_3$, —$CH_2CCl_3$, and the like.

"Heteroalkyl" means an alkyl radical as defined herein wherein one, two or three hydrogen atoms have been replaced with a substituent independently selected from the group consisting of —$OR^a$, —$NR^bR^c$, and —$S(O)_nR^d$ (where n is an integer from 0 to 2), with the understanding that the point of attachment of the heteroalkyl radical is through a carbon atom, wherein $R^a$ is hydrogen, acyl, alkyl, cycloalkyl, or cycloalkylalkyl; $R^b$ and $R^c$ are independently of each other hydrogen, acyl, alkyl, cycloalkyl, or cycloalkylalkyl; and when n is 0, $R^d$ is hydrogen, alkyl, cycloalkyl, or cycloalkylalkyl, and when n is 1 or 2, $R^d$ is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Hydroxyalkyl" means an alkyl radical as defined herein, substituted with one or more, preferably one, two or three hydroxy groups, provided that the same carbon atom does not carry more than one hydroxy group. Representative examples include, but are not limited to, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl, preferably 2-hydroxyethyl, 2,3-dihydroxypropyl and 1-(hydroxymethl)-2-hydroxyethyl. Accordingly, as used herein, the term "hydroxyalkyl" is used to define a subset of heteroalkyl groups.

"Heterosubstituted cycloalkyl" means a cycloalkyl radical as defined herein wherein one, two or three hydrogen atoms in the cycloalkyl radical have been replaced with a substituent independently selected from the group consisting of hydroxy, alkoxy, amino, acylamino, monoalkylamino, dialkylamino, or —S(O)$_n$R (where n is an integer from 0 to 2) such that when n is 0, R is hydrogen, alkyl, cycloalkyl, or cycloalkylalkyl, and when n is 1 or 2, R is alkyl, cycloalkyl, cycloalkylalkyl, amino, acylamino, monoalkylamino, or dialkylamino. Representative examples include, but are not limited to, 2-, 3-, or 4-hydroxycyclohexyl, 2-, 3-, or 4-aminocyclohexyl, 2-, 3-, or 4-sulfonamidocyclohexyl, and the like, preferably 4-hydroxycyclohexyl, 2-aminocyclohexyl, 4-sulfonamidocyclohexyl.

"Heteroalkylsubstituted cycloalkyl" means a cycloalkyl radical as defined herein wherein one, two or three hydrogen atoms in the cycloalkyl radical have been replaced with a heteroalkyl group with the understanding that the heteroalkyl radical is attached to the cycloalkyl radical via a carbon-carbon bond. Representative examples include, but are not limited to, 1-hydroxymethylcyclopentyl, 2-hydroxymethylcyclohexyl, and the like.

"Heteroaryl" means a monovalent monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring is optionally substituted independently with one or more substituents, preferably one or two substituents, selected from alkyl, haloalkyl, heteroalkyl, hydroxy, alkoxy, halo, nitro, cyano, More specifically the term heteroaryl includes, but is not limited to, pyridyl, furanyl, thienyl, thiazolyl, isothiazolyl, triazolyl, imidazolyl, isoxazolyl, pyrrolyl, pyrazolyl, pyrimidinyl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, benzimidazolyl, benzisoxazolyl or benzothienyl, and the derivatives thereof.

"Heteroaralkyl" means a radical —R$^a$R$^b$ where R$^a$ is an alkylene group and R$^b$ is a heteroaryl group as defined herein, e.g., pyridin-3-ylmethyl, imidazolylethyl, pyridinylethyl, 3-(benzofuran-2-yl)propyl, and the like.

"Heterocyclyl" means a saturated cyclic radical of 5 to 8 ring atoms in which one or two ring atoms are heteroatoms selected from NR (where R is independently hydrogen, alkyl, or heteroalkyl), O, or S(O)$_n$ (where n is an integer from 0 to 2), the remaining ring atoms being C, where one or two C atoms may optionally be replaced by a carbonyl group. The heterocyclyl ring may be optionally substituted independently with one, two, or three substituents selected from alkyl, haloalkyl, heteroalkyl, halo, nitro, cyano, hydroxy, alkoxy, amino, monoalkylamino, dialkylamino, —COR (where R is alkyl). More specifically the term heterocyclyl includes, but is not limited to, tetrahydropyranyl, 2,2-dimethyl-1,3-dioxolane, piperidino, N-methylpiperidin-3-yl, piperazino, N-methylpyrrolidin-3-yl, 3-pyrrolidino, morpholino, thiomorpholino, thiomorpholino-1-oxide, thiomorpholino-1,1-dioxide, pyrrolinyl, imidazolinyl, and the derivatives thereof.

"Heteroalkylsubstituted heterocyclyl" means a heterocyclyl radical as defined herein wherein one, two or three hydrogen atoms in the heterocyclyl radical have been replaced with a heteroalkyl group with the understanding that the heteroalkyl radical is attached to the heterocyclyl radical via a carbon-carbon bond. Representative examples include, but are not limited to, 4-hydroxymethylpiperidin-1-yl, 4-hydroxymethylpiperazin-1-yl, 4-hydroxyethylpiperidin-1-yl, 4-hydroxyethylpiperazin-1-yl, and the like.

"Heterocyclylalkyl", "cycloalkylalkyl", or "phenylalkyl" means a radical —R$^a$R$^b$ where R$^a$ is an alkylene group and R$^b$ is phenyl or a heterocyclyl or cycloalkyl group as defined herein, e.g., tetrahydropyran-2-ylmethyl, 4-methylpiperazin-1-ylethyl, 3-piperidinylmethyl, 2,2-dimethyl-1,3-dioxoxolan-4-ylmethyl, benzyl, cyclohexylmethyl, and the like.

"Monoalkylamino" means a radical —NHR where R is an alkyl, cycloalkyl, or cycloalkylalkyl group as defined above, e.g., methylamino, (1-methylethyl)amino, cyclohexylamino, cyclohexylmethylamino, cyclohexylethylamino, and the like.

"Optional" or "optionally" means that the subsequently described event or circumstance may but need not occur, and that the description includes instances where the event or circumstance occurs and instances in which it does not. For example, "heterocycle group optionally mono- or di- substituted with an alkyl group" means that the alkyl may but need not be present, and the description includes situations where the heterocyclo group is mono- or disubstituted with an alkyl group and situations where the heterocyclo group is not substituted with the alkyl group.

"Phenylalkyl" means a radical —R$^a$R$^b$ where R$^a$ is an alkylene group and R$^b$ is a phenyl group as defined herein, e.g., benzyl and the like.

"Hydroxy or amino protecting group" refers to those organic groups intended to protect oxygen and nitrogen atoms against undesirable reactions during synthetic procedures. Suitable oxygen and nitrogen protecting groups are well known in the art e.g., trimethylsilyl, dimethyl-tert-butylsilyl, benzyl, benzyloxy-carbonyl (CBZ), tert-butoxycarbonyl (Boc), trifluoroacetyl, 2-trimethylsilylethanesulfonyl (SES), and the like. Others can be found in the book by T. W. Greene and G. M. Wuts, *Protecting Groups in Organic Synthesis*, Second Edition, Wiley, New York, 1991, and references cited therein.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of Formula (I) may possess one or more asymmetric centers; such compounds can therefore be produced as individual (R)- or (S)-stereoisomers or as mixtures thereof. For example, if the R$^6$ substituent in a compound of formula (I) is 2-hydroxyethyl, then the carbon to which the hydroxy group is attached is an asymmetric center and therefore the compound of Formula (I) can exist as an (R)- or (S)-stereoisomer. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the specification and claims includes both one and more than one such excipient.

A "pharmaceutically acceptable salt" of a compound means a salt that is pharmaceutically acceptable and that possesses the desired pharmacological activity of the parent compound. Such salts include:

(1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-napthalenesulfonic acid, 4-toluenesulfonic acid, camphorsulfonic acid, 3-phenylpropionic acid, trimethylacetic acid, tertiary butylacetic acid, lauryl sulfuric acid, gluconic acid, glutamic acid, hydroxynapthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

A compound of Formula (I) may act as a pro-drug. Prodrug means any compound which releases an active parent drug according to Formula (I) in vivo when such prodrug is administered to a mammalian subject. Prodrugs of a compound of Formula (I) are prepared by modifying functional groups present in the compound of Formula (I) in such a way that the modifications may be cleaved in vivo to release the parent compound. Prodrugs include compounds of Formula (I) wherein a hydroxy, amino, or sulfhydryl group in compound (I) is bonded to any group that may be cleaved in vivo to regenerate the free hydroxyl, amino, or sulfiiydryl group, respectively. Examples of prodrugs include, but are not limited to esters (e.g., acetate, formate, and benzoate derivatives), carbamates (e.g., N,N-dimethylamino-carbonyl) of hydroxy functional groups in compounds of Formula (I), and the like.

"Treating" or "treatment" of a disease includes:
(1) preventing the disease, i.e. causing the clinical symptoms of the disease not to develop in a mammal that may be exposed to or predisposed to the disease but does not yet experience or display symptoms of the disease,
(2) inhibiting the disease, i.e., arresting or reducing the development of the disease or its clinical symptoms, or
(3) relieving the disease, i.e., causing regression of the disease or its clinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

Nomenclature

The naming and numbering of the compounds of Formula (I) is illustrated below.

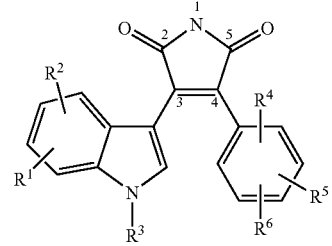

The nomenclature used in this application is generally based on the IUPAC recommendations. Since strict adherence to these reconmmendations would result in the names changing substantially when only a single substituent is changes, compounds have been named in a form that maintains consistency of nomenclature for the basic structure of the molecule. For example, a compound of Formula (I) where $R^1$, $R^2$, $R^4$ and $R^5$ are hydrogen, $R^3$ is methyl, $R^6$ is 2-hydroxyethylamino and is meta to the carbon attaching the phenyl ring to the pyrrole-2, 5-dione ring is named 3-(1-methylindolyl)-4-[3-(2-hydroxyethylaminophenyl)-1H-pyrrole-2,5-dione.

a compound of Formula (I) where $R^1$, $R^2$, $R^4$ and $R^5$ are hydrogen, $R^3$ is methyl, $R^6$ is 2-hydroxyethylamino and is para to the carbon attaching the phenyl ring to the pyrrole-2, 5-dione ring is named 3-(1-methylindolyl)-4-[4-(2-hydroxyethylaminophenyl)-1H-pyrrole-2,5-dione.

Representative Compounds of Formula (I) are as Follows
I. Compounds of Formula (I) where $R^1$, $R^2$, $R^4$ and $R^5$=hydrogen, $R^3$=methyl, and $R^6$ is as defined below are:

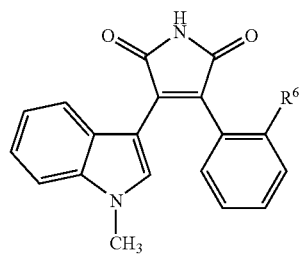

| Cpd. # | $R^6$ | M. pt ° C. | Mass Spec. | Example |
|---|---|---|---|---|
| I-1 | 2,3-dihydroxypropoxy | 245-247.1 | 392 $M^+$ | 1 |
| I-2 | 2,2-dimethyl-1,3-dioxolan-4-ylmethyloxy | 220.8-221.2 | 432 $M^+$ | 2 |

II. Compounds of Formula (I) where $R^1$, $R^2$, $R^4$ and $R^5$=hydrogen, $R^3$=methyl, and $R^6$ is as defined below are:

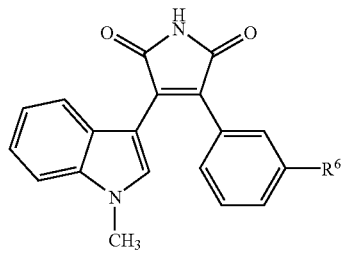

| Cpd. # | $R^6$ | M. pt ° C. | Mass Spec. | Example |
|---|---|---|---|---|
| II-1 | 2-aminoethyloxy hydrochloride | 182.4-187 | 362 M+ | 6 |
| II-2 | 3-aminopropyloxy hydrochloride | | 375 M+ | 5 |
| II-3 | 2(R),3-dihydroxypropoxy | 177.7-178 | 392 M+ | 2 |
| II-4 | 2-morpholin-4-ylethyloxy | 197.7-199 | 431 M+ | 3 |
| II-5 | 2(S),3-dihydroxy-propoxy | 176.9-178.1 | 392 M+ | 2 |
| II-6 | (R)-2,2-dimethyl-1,3-dioxolan-4-ylmethyloxy | | 432 M+ | 1 |
| II-7 | (S)-2,2-dimethyl-1,3-dioxolan-4-ylmethyloxy | 186.8-187.4 | 432 M+ | 1 |
| II-8 | (RS)-2,2-dimethyl-1,3-dioxolan-4-yl-methylamino | | 431 M+ | 7 |
| II-9 | 2,3-dihydroxy-propylamino | 160-163.5 | 392(M + H)+ | 7 |
| II-10 | 2,2-dimethyl-1,3-dioxan-5-ylamino | 201-203 | 431 M+ | 9 |
| II-11 | (RS)-2-hydroxy-1-hydroxymethylethylamino | 97.5-101 | 391 M+ | 10 |
| II-12 | (RS)-3-hydroxybutylamino | | 389 M+ | 14 |
| II-13 | (RS)-2-hydroxy-1-methylpropylamino | | 389 M+ | 15 |
| II-13A | tetrahydropyran-4-ylamino | | 401 M+ | 8 |
| II-14 | imidazol-2-ylmethylamino | | 397 M+ | 11 |
| II-15 | morpholin-4-yl hydrochloride | 205.3-212.6 | 388 M+ | 4 |
| II-16 | 3-(tert-butyl-dimethylsilyl-oxy)propylamino | 58-65 | 490(M + H)+ | 12 |
| II-17 | 2-(tert-butyl-diphenylsilyl-oxy)ethylamino | | 600(M + H)+ | 12 |
| II-18 | 3-hydroxypropylamino hydrochloride | 180-192 | 376(M + H)+ | 13 |
| II-19 | 2-hydroxyethylamino hydrochloride | 170.3-170.6 | 362(M + H)+ | 13 |
| II-20 | 3-hydroxypropyloxy | 150.2-152.6 | 377(M + H)+ | 13 |
| II-21 | 3-(tert-butyl-dimethylsilyl-oxy)propyloxy | 151.2-151.7 | 491(M + H)+ | 6 |
| II-22 | (RS)-1-hydroxymethylethyl-amino | 203.1-205.8 | 376(M + H)+ | 15 |
| II-23 | 3-hydroxy-1-methylpropylamino | | 389 M+ | 14 |
| II-24 | (RS)-bis(2,3-dihydroxy-propyl)amino | | 466(M + H)+ | 7 |
| II-25 | pyrrolidin-1-yl | | 372 M+ | 4 |
| II-26 | (S)-2-hydroxy-2-hydroxymethylethylamino | | 392(M + H)+ | 7 |
| II-27 | 2(R),3-dihydroxy-propylamino•HCl | | 392(M + H)+ | 7 |
| II-28 | 4-hydroxycyclohexylamino | | 415 M+ | 8 |
| II-29 | 4-hydroxypiperidin-1-yl | 136.0-141.0 | 402(M + H)+ | 23 |
| II-30 | (R)-2,2-dimethyl-1,3-dioxolan-4-yl-methylsulfanyl | | 448 M+ | 18 |
| II-31 | (R)-2,3-dihydroxypropylsulfanyl | | 408 M+ | 21 |
| II-32 | (R)-2,2-dimethyl-1,3-dioxolan-4-yl-methylsulfinyl | | 465(M + H)+ | 19 |
| II-33 | (R)-2,3-dihydroxypropylsulfinyl | | 425(M + H)+ | 21 |
| II-34 | (R)-2,2-dimethyl-1,3-dioxolan-4-yl-methylsulfonyl | | 481(M + H)+ | 20 |
| II-35 | (R)-2,3-dihydroxypropylsulfonyl | | 411(M + H)+ | 21 |

III. Compounds of Formula (I) where $R^2$, $R^4$ and $R^5$=hydrogen, $R^1$, $R^3$ and $R^6$ are as defined below are:

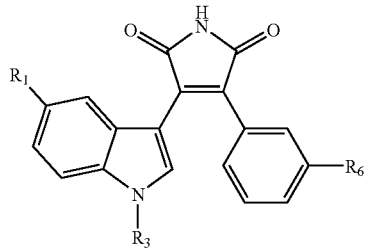

| Cpd. # | $R^1$ | $R^3$ | $R^6$ | M. pt °C. | Mass Spec. | Example |
|---|---|---|---|---|---|---|
| III-1 | Chloro | methyl | (RS)-2,3-dihydroxypropylamino | 224.5-225.7 | 426(M + H)+ | 16 |
| III-2 | fluoro | methyl | 3-aminopropyloxy hydrochloride | 223.2-225.0 | 410(M + H)+ | 17 |
| III-3 | H | H | 2-(morpholin-4-yl)-ethoxy | | 417(M + H)+ | 3 |
| III-4 | chloro | methyl | ((R)-2-hydroxy-2-hydroxymethyl)ethyloxy | | 427(M + H)+ | 24 |
| III-5 | fluoro | methyl | ((R)-2-hydroxy-2-hydroxymethyl)ethyloxy | | 411(M + H)+ | 24 |
| III-6 | fluoro | 3-hydroxy-propyl | (RS)-2,3-dihydroxy-propylamino | | 454(M + H)+ | 22 |
| III-7 | methoxy | methyl | 2,3-dihydroxy-propylamino | | 421 | 25 |
| III-8 | methyl | methyl | 2,3-dihydroxy-propylamino | | 405 | 25 |
| III-9 | isopropoxy | methyl | 2,3-dihydroxy-propylamino | | 449 | 26 |

IV. Compounds of Formula (I) where $R^1$, $R^2$, $R^4$ and $R^5$=hydrogen, $R^3$=methyl, and $R^6$ is as defined below are:

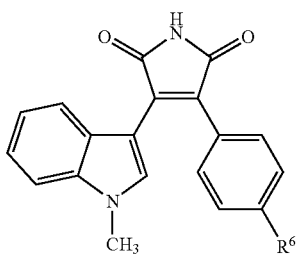

| Cpd. # | $R^6$ | m. pt °C. | Mass Spec. | Example |
|---|---|---|---|---|
| IV-1 | (R)-2,2-dimethyl-1,3-dioxolan-4-yl-methyloxy | | 432 M+ | 1 |
| IV-2 | (RS)-2,3-dihydroxy-propylamino | 212-213.5 | | 7 |
| IV-3 | (RS)-2,2-dimethyl-1,3-dioxolan-4-yl-methylamino | 85-87.8 | | 7 |
| IV-4 | 3-hydroxybutylamino | 58-61.5 | 389 M+ | 13 |
| IV-5 | (RS)-1-methyl-2-hydroxyethylamino | | 375 | 15 |
| IV-6 | 2(R),3-dihydroxypropoxy | 220.3-222.7 | 392 M+ | 1 |

V. Additional compounds of Formula (I) where only one of $R^4$-$R^6$ is hydrogen are:

3-(1-methyl-indol-3-yl)-4-{3-((R)-2,3-dihydroxy-propoxyl)-2-methylphenyl}-1H-pyrrole2,5-dione; and 3-(1-methyl-indol-3-yl)-4-{3-((R)-2,3-dihydroxy-propoxyl)-2-nitrophenyl}-1H-pyrrole-2,5-dione.

3-(1-methylindol-3-yl)-4-[5-((R)-2,3-dihydroxypropoxy)-2-nitrophenyl]-1H-pyrrole-2,5-dione.

Compounds of Formula (I) are made by the methods of copending U.S. patent application Ser. No. 09/916,706 filed Jul. 27, 2001 incorporated by reference herein.

Compounds of Formula I are useful increasing bone formation as described herein. Other compounds useful in these methods are described in WO99/65897 (U.S. Pat. No. 6417185 (Chiron)), WO 01/20727A1 (U.S. Pat. No. 6361346 (Sanofi-Synthelabo)), EP 1 136 493 A1(Sanofi-Synthelabo), EP 1 136 489 A1(Sanofi-Synthelabo), EP 1 136 486 A1 (Sanofi-Synthelabo), EP 1 136 483 A1(Sanofi-Synthelabo), EP 1 136 099A1 (Sanofi-Synthelabo), ) WO 2000/021927 (SKB), WO 2001/049709, WO 2001/056567 (US 2001039275 (Novo Nordisk)), WO 2001/081345, WO 2001/085685, WO 2001/009106 (SKB) and WO2001/52862 (U.S. Pat. No. 6,323,029 (Isis)), WO2001/37819, WO2001/60374, EP 1 106 180A1 (CNRS), WO2000/38675 (SKB), WO 2002096905 (Vertex), WO 2002088078 (Vertex), WO 2002085909, US 2002156087, US 2002147146, WO 2002079197, WO 2002066480, WO 2002065979, WO 2002062795, WO 2002062789, WO 2002059112, WO 2002050079, WO 2002050073, WO 2002050066, WO 2002032896, WO 2002024694, WO 2002022604, WO 2002020495, WO 2002018346, EP 1184385, EP 1184384, EP 1184383 and WO 2001085685, all incorporated by reference.

A particular compound that is useful in the methods described herein is $N^6$-{2-[4-(2,4-dichloro-phenyl)-5-(1H-imidazol-2-yl)-pyrimidin-2-ylamino]-ethyl}-3-nitro-pyridine-2,6-diamine hydrochloride prepared as described in WO99/65897.

Utility, Testing, and Administration

Utility

Applicants have unexpectedly discovered that a variety of structurally dissimilar compounds that share the common feature of being GSK-3β inhibitors are effective in increasing bone formation. Thus, the methods disclosed herein provide treatments for increasing bone mineral density, forming new bone, increasing the rate of fracture healing, improving the mechanical properties of bone (i.e., forming cortical and trabecular bone) and treating osteoporosis, iatrogenic and senile osteoporosis and related bone metabolic diseases.

Treatment with GSK-3β inhibitors is useful in the treatment of Type I (postmenopausal), Type II (iatrogenic), and Type III (senile) osteoporosis, including that associated with corticosteroid treatment (e.g. for asthma), with chemotherapy, as well in the treatment of osteodystrophy due to renal dialysis, and hyperparathyroidism. Treatment with GSK-3β inhibitors as described herein results in increased bone mineral density and unlike conventional treatments provides bone of good quality. Therefore, the treatments described herein may reduce the incidence of fracture and result in faster healing of pre-existing fractures. Such treatments are particularly useful for patients suffering from estrogen withdrawal (e.g. elderly females) who would otherwise be at risk for an increased fracture rate. Types of fractures treatable include both traumatic and osteoporotic fractures, e.g., fractures of the hip, neck of the femur, wrist, vertebrae, spine, ribs, sternum, larynx and trachea, radius/ulna, tibia, patella, clavicle, pelvis, humerus, lower leg, fingers and toes, face and ankle.

Testing

Identification of compounds that inhibit GSK 3β may be done by in vitro assays such as ligand binding assay and inhibition of β-catenin degradation assay as described in detail in Biological Example 1 and 2 below.

Administration and Pharmaceutical Composition

In general, the GSK-3β inhibitors will be administered in a therapeutically effective amount by any of the accepted modes of administration for agents that are used to increase bone formation. The actual amount of the inhibitor will depend upon numerous factors such as the severity of the disease to be treated, the age and relative health of the subject, the potency of the compound used, the route and form of administration, and other factors. The inhibitor can be administered more than once a day, preferably once or twice a day.

Therapeutically effective amounts of GSK-3β inhibitors may range from approximately 1 mg to 50 mg per kilogram body weight of the recipient per day; preferably about 3 mg/kg/day. Thus, for administration to a 70 kg person, the dosage range would be about 70 to 3500 mg/day, most preferably be about 200 mg per day.

In general, the GSK-3βinhibitors will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen which can be adjusted according to the degree of affliction. Compositions can take the form of tablets, pills, capsules, semisolids, powders, sustained release formulations, solutions, suspensions, elixirs, aerosols, or any other appropriate compositions.

A related aspect of this invention relates to combination therapies of GSK-3β inhibitors for increased bone formation with other active agents such as bisphosphonates, estrogen, SERMS (selective estrogen receptor modulators), calcitonins or anabolic therapies. Examples of bisphosphonates include alendronate, ibandronate, pamidronate, etidronate and risedronate. Examples of SERMS include raloxifene, dihydroraloxifene and lasofoxifene. Calcitonins include human and salmon calcitonin. Anabolic agents include parathyroid hormones (PTH) e.g. hPTH(1-34), PTH(1-84), and parathyroid hormone-related protein (PTHrP) and analogs thereof. Particular analogs of PTHrP are described in "Mono- and Bicyclic Analogs of Parathyroid Hormone-Related Protein. 1. Synthesis and Biological Studies," Michael Chorev et al. Biochemistry, 36:3293-3299 (1997) and "Cyclic analogs of PTH and PTHrP," WO 96/40193 and U.S. Pat. No. 5,589,452 and WO 97/07815. The other active agent may be administered concurrently, prior to or after the GSK-3β inhibitor and may be administered by a different delivery method. Preferably, the GSK-3β inhibitor is administered first. The period of this administration may be of any length, but typically ranges from six to twenty four months. This treatment is then followed by treatment with an antiresorptive agent, e.g., a bisphosphonate, SERM, calcitonin or hormone replacement therapy.

Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The pharmaceutical compositions of GSK 3β inhibitors usually contain at least one pharmaceutically acceptable excipient. Acceptable excipients are non-toxic, aid administration, and do not adversely affect the therapeutic benefit of the inhibitor. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc.

Preferred liquid carriers, particularly for injectable solutions, include water, saline, aqueous dextrose, and glycols.

Pharmaceutical Sciences, edited by E. W. Martin (Mack Publishing Company, 18th ed., 1990).

The amount of the compound in a formulation can vary within the full range employed by those skilled in the art. Typically, the formulation will contain, on a weight percent (wt %) basis, from about 0.01-99.99 wt % of a GSK-3 β inhibitor based on the total formulation, with the balance being one or more suitable pharmaceutical excipients. Preferably, the compound is present at a level of about 1-80 wt %. ow.

EXAMPLES

The following preparations and examples are given to enable those skilled in the art to more clearly understand and to practice the present invention. They should not be considered as limiting the scope of the invention, but merely as being illustrative and representative thereof.

Abbreviations used in the examples are defined as follows: "HCl" for hydrochloric acid, "DMF" for dimethylformamide, "NaOH" for sodium hydroxide, "KOH" for potassium hydroxide, "DMSO" for dimethylsulfoxide, "NaHCO$_3$" for sodium bicarbonate, "NaCl" for sodium chloride, "K$_2$CO$_3$" for potassium carbonate, "Na$_2$CO$_3$" for sodium carbonate, "LiOH" for lithium hydroxide, "Et$_3$N" for triethylamine, "NH$_3$ (aq)" for ammonium hydroxide, "CH$_2$Cl$_2$" for methylene chloride, "MeOH" for methanol, "EtOH" for ethanol, "Ph$_3$P" for triphenylphosphine, "CsCO$_3$" for cesium carbonate, "BINAP" for 2,2-bis-(diphenylphosphino)-1,1'-binaphthyl, "Pd$_2$(dba)$_3$" for tris(dibenzylideneacetone)-dipalladium, "NaCNBH$_3$" for sodium cyanoborohydride, "THF" for tetrahydrofuran, "Na$_2$SO$_4$" for sodium sulfate, "RT" for room temperature, "PTLC" for preparatory thin layer chromatography, "SiO$_2$" for silica gel, "EtOAc" for ethyl acetate, "APMA" for aminophenyl-mercuric acetate, "IL-1" for interleukin-1, and "RPMI" for Roswell Park Memorial Institute.

Synthetic Examples

Examples 1-3 Show Methods of Making Specific Compounds of Formula (I).

Example 1

Synthesis of 3-(1-methylindol-3-yl)-4-[3-(3-tert-butyldimethylsilyloxypropylamino)phenyl]-1H-pyrrole-2,5-dione

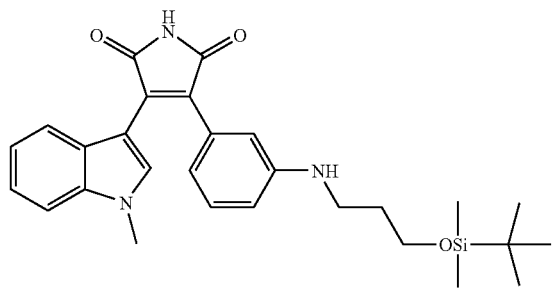

Step 1

Tetrapropylammonium perruthenate (0.18 g, 5.3 mmol) was added to a mixture of methylene chloride (20 mL) and acetonitrile (2 mL) containing 3-(tert-butyldimethylsilyloxy)-propanol (2 g, 0.01 mmol), N-methylmorpholine N-oxide (1.76 g) and 4 Å molecular sieves. The reaction mixture was stirred at RT overnight and then filtered through a pad of silica gel. The filtrate was concentrated under vacuo to afford 3-(tert-butyldimethylsilyloxy)-propionaldehyde (1.3 g, 66%).

Step 2

A mixture of 3-(1-methylindol-3-yl)-4-(3-aminophenyl)-1H-pyrrole-2,5-dione (0.2 g, 6 mmol) and 3-(tert-butyldimethylsilyloxy)propionaldehyde (0.25 g,13 mmol) in CH$_2$Cl$_2$ (10 mL) and MeOH (5 mL) was stirred at room temperature for 15 min and then NaCNBH$_3$ (57 mg, 1.5 eq) was added. The reaction mixture was stirred at RT overnight and then concentrated under vacuo. The residue was purified by preparatory TLC to give 98 mg 3-(1-methylindol-3-yl)-4-[3-(3-tert-butyldimethylsilyloxypropylamino)phenyl]-1H-pyrrole-2,5-dione (32%) MS (LSIMS): (M+H)$^+$ 490, MP: 58-65° C.

Proceeding as described in example 1 above, but substituting 3-(tert-butyldimethyl-silyloxy)propanol with 2-(tert-butyldiphenylsilyloxy)ethanol provided 3-(1-methylindol-3-yl)-4-[3-(3-tert-butyldiphenylsilyloxy-ethylamino)phenyl]-1 H-pyrrole-2,5-dione.

Example 2

Synthesis of 3-(1-methyl-5-chloroindol-3-yl)-4-{3-[((RS)-2,3-dihydroxypropylamino]phenyl}-1H-pyrrole-2,5-dione

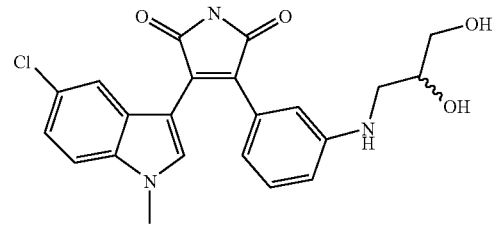

Step 1

To room temperature solution of 5-chloroindole (4.97 g) in dry DMF (40 mL) was added potassium hydroxide pellets (2.76 g) and stirred 1 h until most of the solid dissolved. The resulting mixture was cooled to 0° C. in an ice bath and iodomethane (2.45 mL) was added dropwise and later stirred overnight at room temperature under argon. The reaction mixture was poured into water and extracted twice with ETOAc. The combined ETOAc portions were combined, washed with water, dried over magnesium sulfate, concentrated, and flash chromatographed with 10% ETOAc/Hexane to give 1-methyl-5-chloroindole as a pink liquid (5.43 g).

Step 2

1-Methyl-5-chloroindole-3-glyoxylyl chloride was prepared by proceeding as described in Example 1, Step 1, but substituting 1-methyl-5-chloroindole for 1-methylindole.

Step 3

3-(1-Methyl-5-chloroindol-3-yl)-4-(3-nitrophenyl)furan-2,5-dione was prepared by proceeding as described in Example 1, Step 2, but substituting 1-methyl-5-chloroindole-3-glyoxylyl chloride for 1-methylindole-3-glyoxylyl chloride.

Step 4

3-(1-Methyl-5-chloroindol-3-yl)-4-(3-nitrophenyl)-1H-pyrrole-2,5-dione was prepared by proceeding as described in Example 1, Step 3, but substituting 3-(1-methyl-5-chloroindol-3-yl)-4-(3-nitrophenyl)furan-2,5-dione for 3-(1-methylindol-3-yl)-4-(3-nitrophenyl)furan-2,5-dione.

Step 5

A mixture of 3-(1-methyl-5-chloroindol-3-yl)-4-(3-nitrophenyl)-1H-pyrrole-2,5-dione (865 mg), 10% palladium on carbon (90 mg), and glacial HOAc (35 mL) was stirred and hydrogenated at atmospheric pressure using a balloon (2 h). The reaction mixture was filtered through a pad of celite, cooled to 0° C. and KOH pellets were added until pH 8. The solution was extracted with ETOAc, dried (magnesium sulfate), and stripped. The crude was flash chromatographed with 10% through 20% ETOAc-Hexane to provide 3-(1-methyl-5-chloroindol-3-yl)-4-(3-aminophenyl)-1H-pyrrole-2,5-dione (495 mg).

Step 6

To a room temperature solution of 3-(1-methyl-5-chloroindol-3-yl)-4-(3-aminophenyl)-1H-pyrrole-2,5-dione (492 mg) in methanol (250 mL) was added DL-glyceraldehyde dimer dissolved in water (15 mL) followed by sodium cyanoborohydride (110 mg) and the reaction mixture was stirred overnight under argon. The reaction appeared to be only 30% complete by TLC. Additional dimer (150 mg) and cyanoborohydride (100 mg) were added. After another 6 h, the reaction appeared to be 50% complete. The solvent was removed and the crude residue was flash chromatographed with 5% to 7% to 10% MeOH/dichloromethane. 3-(1-Methyl-5-chloroindol-3-yl)-4-{3-[((RS)-2,3-dihydroxypropylamino]phenyl}-1H-pyrrole-2,5-dione was obtained as a dark red solid (220 mg). MS(EI): (M+H)$^+$ 426. M. pt. 224.8-226.1° C.

Example 3

Synthesis of 3-(1-methyl-5-fluoroindol-3-yl)-4-{3-[((RS)-2,3-dihydroxy-propylamino]phenyl}-1H-pyrrole-2,5-dione

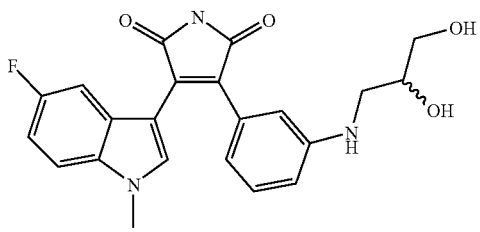

Step 1

1-Methyl-5-fluoroindole was prepared by proceeding as described in Example 2, Step 1, but substituting 5-fluoroindole for 5-chloroindole.

Step 2

1-Methyl-5-fluoroindole-3-glyoxylyl chloride was prepared by proceeding as described in Example 2, Step 2, but substituting 1-methyl-5-fluoroindole for 1-methyl-chloroindole.

Step 3

3-(1-Methyl-5-fluoroindol-3-yl)-4-(3-nitrophenyl)furan-2,5-dione was prepared by proceeding as described in Example 2, Step 3, but substituting 1-methyl-5-fluoroindole-3-glyoxylyl chloride for 1-methyl-5-chloroindole-3-glyoxylyl chloride.

Step 4

3-(1-Methyl-5-fluoroindol-3-yl)-4-(3-nitrophenyl)-1H-pyrrole-2,5-dione was prepared by proceeding as described in Example 2, Step 3, but substituting 3-(1-methyl-5-fluoroindol-3-yl)-4-(3-nitrophenyl)furan-2,5-dione for 3-(1-methyl-5-chloroindol-3-yl)-4-(3-nitrophenyl)furan-2,5-dione.

Step 5

3-(1-Methyl-5-fluoroindol-3-yl)-4-(3-aminophenyl)-1H-pyrrole-2,5-dione was prepared by proceeding as described in Example 2, Step 5, but substituting 3-(1-3-(1-methyl-5-fluoroindol-3-yl)-4-(3-nitrophenyl)-1H-pyrrole-2,5-dione for 1-methyl-5-chloroindol-3-yl)-4-(3-nitrophenyl)-1H-pyrrole-2,5-dione.

Step 6

3-(1-methyl-5-fluoroindol-3-yl)-4-{3-[((RS)-2,3-dihydroxypropylamino]phenyl}-1H-pyrrole-2,5-dione was prepared by proceeding as described in Example 2, Step 5, but substituting 3-(1-methyl-5-fluoroindol-3-yl)-4-(3-aminophenyl)-1H-pyrrole-2,5-dione for 3-(1-methyl-5-chloroindol-3-yl)-4-(3-aminophenyl)-1H-pyrrole-2,5-dione. MS(EI) (M+H)$^+$ 410, MP: 223.2°-250°.

Formulation Examples

The following are representative pharmaceutical formulations containing a compound of Formula (I).

Example 1

Tablet Formulation

The following ingredients are mixed intimately and pressed into single scored tablets.

| Ingredient | Quantity per tablet, mg |
|---|---|
| compound of this invention | 400 |
| cornstarch | 50 |
| croscarmellose sodium | 25 |
| lactose | 120 |
| magnesium stearate | 5 |

Example 2

Capsule Formulation

The following ingredients are mixed intimately and loaded into a hard-shell gelatin capsule.

| Ingredient | Quantity per capsule, mg |
|---|---|
| compound of this invention | 200 |
| lactose, spray-dried | 148 |
| magnesium stearate | 2 |

Example 3

Suspension Formulation

The following ingredients are mixed to form a suspension for oral administration.

| Ingredient | Amount |
| --- | --- |
| compound of this invention | 1.0 g |
| fumaric acid | 0.5 g |
| sodium chloride | 2.0 g |
| methyl paraben | 0.15 g |
| propyl paraben | 0.05 g |
| granulated sugar | 25.0 g |
| sorbitol (70% solution) | 13.00 g |
| Veegum K (Vanderbilt Co.) | 1.0 g |
| flavoring | 0.035 mL |
| colorings | 0.5 mg |
| distilled water | q.s. to 100 mL |

Example 4

Injectable Formulation

The following ingredients are mixed to form an injectable formulation.

| Ingredient | Amount |
| --- | --- |
| compound of this invention | 0.2 mg-20 mg |
| sodium acetate buffer solution, 0.4 M | 2.0 mL |
| HCl (1N) or NaOH (1N) | q.s. to suitable pH |
| water (distilled, sterile) | q.s. to 20 mL |

Example 5

Suppository Formulation

A suppository of total weight 2.5 g is prepared by mixing the compound of the invention with Witepsol® H-15 (triglycerides of saturated vegetable fatty acid; Riches-Nelson, Inc., New York), and has the following composition:

| | |
| --- | --- |
| compound of the invention | 500 mg |
| Witepsol ® H-15 | balance |

Biological Examples

Example 1

Inhibition of Glycogen Synthase Kinase-3β-in vitro Assay

The in vitro GSK-3β inhibitory activity of compounds of this invention was determined with a truncated form of recombinant rabbit GSK-3β enzyme.

Isolation of GSK-3β

The construct was cloned in pGEX-3X vector according to the procedure described in Wang, Q. M. et al., *J. Biol. Chem.* 269, 14566-14574 (1994). Ten amino acids at the N-terminus were deleted to obtain constitutively active GSK-3β ((see Murai H. et al., *FEBS Lett.* 392,153-60, (1996)). GSK-3β was expressed in BL21 DE3 cells. The cells were grown at 37° C. until they reached mid log phase and then induced with isopropyl-beta-(D)-thiogalactopyranoside (final concentration 0.4 mM) at 30° C. for 2 h. The cells were homogenized and the cell extract was loaded on a glutathione sepharose 4B column. GSK-3β was eluted with glutathione buffer (50 mM Tris pH 8 and 10 mM reduced glutathione). The eluate was collected in 3 minute fractions and assayed for GSK-3β content on a 10% SDS PAGE (polyacrylamide gel electrophoresis). Fractions above 20% peak height were pooled, aliquoted, and stored at −80° C. until used.

Inhibition of GSK-3β

The GSK-3β binding assay was performed in 50 μl reactions in a 96 well polypropylene plate, each reaction containing 20 mM magnesium chloride, 40 μM ATP, 2 mM DTT, 88.5 μM biotinylated and phosphorylated CREB-peptide substrate (biotin-KRREILSRRPS($PO_4$)YR-OH, see Wang, Q. M. et al., *J. Biol. Chem.* 269, 14566-14574 (1994)), [γ-$^{33}$P] ATP (1 μCi), and 2 μl of compounds of this invention in DMSO (various concentrations). 15 μl of GSK-3β (various concentrations) was added and the reaction mixture was incubated at 30° C. for 1 h. The reaction was stopped by transferring 25 μl of the reaction mixture to a phosphocellulose plate containing 130 μl of 1.85% phosphoric acid. The free radionucleotides in the membrane were washed off under vacuum with 1.85% phosphoric acid (5 times). After the last wash, the plate was transferred to an adaptor plate and 50 μl of scintillation cocktail (Microscint-20, Packard, cat. #20-133) was added to each well and the amount of radioactivity was counted in a top counter.

Compounds of this invention were active in this assay.

The GSK-3β inhibitory activities (expressed as $IC_{50}$, the inhibitor concentration causing 50% inhibition of the activity in the control) of some compounds of the invention disclosed in Table I-IV were less than 2 μm. Activities of certain specific compounds are shown below

| Compound | $IC_{50}$ μM |
| --- | --- |
| I-1 | 0.194 |
| II-1 | 0.02 |
| II-2 | 0.0264 |
| II-3 | 0.0032 |
| II-4 | 0.0296 |
| II-9 | 0.0015 |
| III-2 | 0.0007 |
| III-3 | 0.23 |
| IV-1 | 0.1334 |

Example 2

Inhibition of β-catenin Degradation—in Vitro Assay

The cell based GSK-3β activity of compounds of this invention was determined by measuring β-catenin levels in Jurkat T-cells after treatment with the compounds of this invention using ELISA as follows.

Jurkat cells (5×105 cells/mL) were plated in 6-well plates (6 mL/well) and then treated with various concentrations of the compounds of this invention (preferrably 1 nM-10 μM) for 24 h. At the end of the incubation, the cells were collected and washed once with PBS. The cells were then suspended in 0.3 mL RadioImmuno Precipitation Assay lysis (RIPA)

buffer (Boehringer Mannheim, cat.#1 920 693). After 3 freeze—thaw cycles, the cell extracts were centrifuged at 15,000 rpm for 10 min. The supernatant was collected and analyzed using ELISA assay as described below.

96 Microwell plates were coated overnight with capture antibody (mouse monoclonal anti-β-catenin, Zymed La., cat.# 13-8400, 100 µl per well, containing 250 ng antibody) diluted in coating buffer (0.1 M NaHCO$_3$, pH 9.5). The wells were aspirated and washed 3 times with 300 µl of wash buffer (PBS containing 0.05% Tween 20) and blocked with 200 µl of assay diluent (PBS, 10% RBS, pH 7; PharMingen) and then incubated at room temperature for at least 72 h. The wells were washed again as described above. 100 t of the Jurkat cell supernatant and various concentrations of a β-catenin standard (Behrens et al. *Nature*, Vol. 382, p 638 (1996)) were added to the wells and incubated for 2 h at room temperature. After incubation, the wells were washed and 100 µl of anti-β-catenin antibody (Santa Cruz, β-catenin H-102, sc-7199, rabbit IgG) diluted in assay diluent (1:1250) was added to each well and the cells were incubated at room temperature for 2 h. After washing, 100 µl of working detector (Sigma B5283, mouse monoclonal anti-rabbit IgG-Biotin) diluted in assay diluent (1:2000) was added into each well and incubated for 1 h at room temperature. 3,3',5,5'-Tetramethylbenzidine (PharMingen, Cat. #2642KK) was used for color development. The reaction was stopped by adding 50 µl of stop solution (2N H$_2$SO$_4$) to each well. The plates were read with an ELISA plate reader at 570 nm within 30 min., of stopping the reaction.

The level of GSK-3β inhibition was calculated by plotting the compound concentration versus β-catenin levels. The results are shown in FIG. 1, confirming the effect of compounds of this invention on β-catenin levels.

Example 3

Study GSK8—Bone Formation in Rats Treated with Compound II-3

Ovalbumin-sensitized Brown-Norway rats were used. They were sensitized i.p. with 100 µg of OA (ovalbumin) in 0.2 ml alum once every week for three weeks (Day 0, 7 and 14). Seven days after the final sensitization (Day 21), rats were challenged with 1% OA for 45 minutes and euthanized 72 hrs later (day 24). Compound II-3 was given twice daily by oral gavage on Days 6-8 and Days 13-23. Compound was prepared as a liposome formulation—8 mg/ml liposome solution in a liposome composition of 1.44 grams of compound and 54 grams of L-alpha-phosphatidylcholine in 160 ml of sterile water for injection.

Femur samples were decalcified in 10% formic acid, embedded in paraffin, sectioned at five micron thickness and stained with hematoxylin and eosin. The animals had moderate increases in cancellous bone under the growth plate of the femur as evaluated by light microscopy.

Example 4

Study MT021 Bone Formation in Rats With Compound II-9

Compound was formulated as a solution in 10% w/v Solutol. Male Wistar rats were dosed by oral gavage, once per day for 14 days at 25, 75 or 150 mg/kg/day and compared to vehicle control (10% Solutol, 10 ml/kg/day). Complete necroscopies were done and the tissues preserved in 10% formalin. Femur, sternum and vertabra were processed and analyzed as described in Example 3. Increased cancellous bone was observed in all groups—only one animal in the 25 mg/kg group. Five out of six rats in the 150 mg/kg group had increased new bone formation, a more intensive and active effect.

Example 5

Bone Anabolism in the Rat

Two structurally dissimilar GSK-3β inhibitors III-2 and N$^6$-{2-[4-(2,4-dichloro-phenyl)-5-(1H-imidazol-2-yl)-pyrimidin-2-ylamino]-ethyl}-3-nitro-pyridine-2,6-diamine (Compound X) were tested for bone anabolic activity in the osteopenic rat model. Three month old rats are ovariectomized (Ovx) and administered either bovine parathyroid hormone (Amino Acids$^{1-34}$) (bPTH in Table) or one of the compounds of the present invention once a day by mouth starting at least 4 weeks post-ovariectomy and continuing until final sacrifice after 3 weeks of daily treatment. Control groups, both sham (rats that were not ovariectomized) and Ovx, received vehicle only. Bovine parathyroid hormone, bPTH, was tested at 40 ug/kg (optimal dose) as an internal positive control for anabolic activity. The effect on III-2 was also tested in intact Sham animals. Blood and urine samples were collected at 2-3 weeks after initiation of treatment and the amount of calcium in the serum and urine was determined.

The bone mineral density of the right femur was determined using the High Resolution Software on a QDR-4500W Bone Densitometer™ (Hologic, Waltham, Mass.). The animals were scanned by placing them on a plexiglass block in a supine position such that the right leg was perpendicular to the main body and the tibia was perpendicular to the femur. The increase in the bone mineral density and the amount of calcium in the urine and the serum for the compounds are given in the table below. Efficacy was observed for both compounds at doses which were not associated with hypercalcemia or hypercalciuria. Similar results were observed in the tibia.

| CPD # | Surgery | Treatment | Dose mg/kg/day | LUMBAR SPINE % 3 wk BMD Change | WHOLE FEMUR % 3 wk BMD Change | Serum Calcium mg/dl | Urine Calcium/ Creatinine mg/mmol |
|---|---|---|---|---|---|---|---|
| III-2 | Sham | Vehicle | 0 | 3.2 ± 2.0 | 6.0 ± 0.8 | 10.5 + 0.1 | 0.230 + 0.035 |
|  | Ovx | Vehicle | 0 | 3.4 ± 1.4 | 4.5 ± 1.1 | 10.1 + 0.1 ++ | 0.145 + 0.026 |
|  | Ovx | bPTH | 0.04 | 12.2 ± 1.5 ++** | 16.6 ± 0.9 ++** | 10.2 + 0.1 ++ | 0.171 + 0.013 |

| CPD # | Surgery | Treatment | Dose mg/kg/ day | LUMBAR SPINE % 3 wk BMD Change | WHOLE FEMUR % 3 wk BMD Change | Serum Calcium mg/dl | Urine Calcium/ Creatinine mg/mmol |
|---|---|---|---|---|---|---|---|
|  | Ovx | Ro330-3544 | 30 | 7.9 ± 1.8 | 11.6 ± 0.9 ++** | 10.1 + 0.1 ++ | 0.109 + 0.056 ++ |
| III-2 | Sham | Vehicle | 0 | 7.6 ± 1.7 | 7.8 ± 1.5 | 10.3 + 0.2 | 0.070 + 0.013 |
|  | Sham | bPTH | 0.04 | 15.7 ± 0.8 ++** | 11.7 ± 1.0 | 10.1 + 0.3 | 0.085 + 0.013 |
|  | Sham | Ro330-3544 | 30 | 9.5 ± 1.8 | 13.1 ± 1.3 ++ | 10.2 + 0.1 | 0.041 + 0.005 + |
| X | Sham | Vehicle | 0 | −2.3 ± 0.8 | 0.4 ± 1.0 | 11.0 + 0.1 ** | 0.169 + 0.011 ** |
|  | Ovx | Vehicle | 0 | −3.5 ± 1.6 | −0.9 ± 0.7 | 10.4 + 0.1 ++ | 0.083 + 0.010 ++ |
|  | Ovx | bPTH | 0.04 | 8.6 ± 1.8 ++** | 7.0 ± 1.1 ++** | 11.0 + 0.2 ** | 0.108 + 0.015 ++ |
|  | Ovx | Ro4387492 | 75 | 3.0 ± 1.3 +** | 3.0 ± 1.4 * | 10.4 + 0.1 ++ | 0.045 + 0.006 ++* |

**p ≦ 0.01,
*p ≦ 0.5 vs OVX control treated with the same vehicle.
++p ≦ 0.01,
'+p ≦ 0.05 vs SHAM control treated with the same vehicle.

The Table below shows the GSK-3β inhibitors used in Examples 3-5 and their IC50's in the GSK-3β assay of Biological Example 1

| Cpd. Number | Structure | IC50 (nM) |
|---|---|---|
| III-2 | 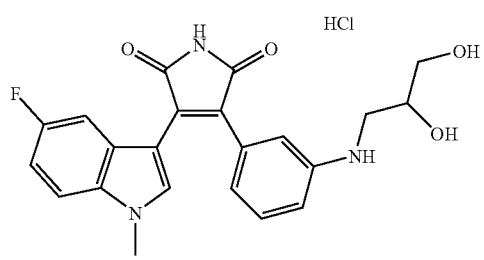 | 0.7 |
| II-3 | 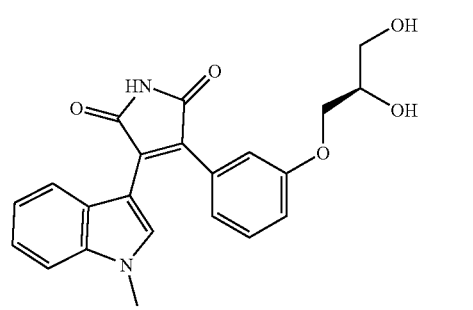 | 3.2 |
| II-0 | 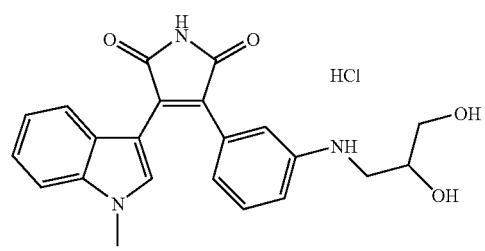 | 1.5 |

-continued

| Cpd. Number | Structure | IC50 (nM) |
|---|---|---|
| Compound X | 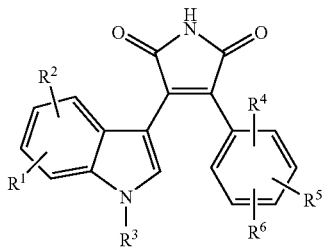 | 1.7 |

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed:

1. A method of treating a bone fracture in a mammal comprising:
    administering to a mammal having a bone fracture an effective amount of a GSK-3β inhibitor of Formula (I)

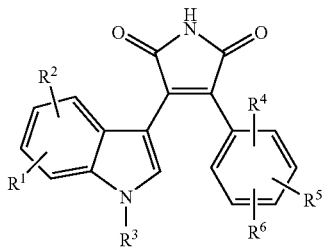

wherein:
    $R^1$ and $R^2$ independently represent hydrogen, alkyl, halo, haloalkyl, alkylthio, hydroxy, alkoxy, cyano, nitro, amino, acylamino, monoalkylamino, or dialkylamino;
    $R^3$ represents hydrogen, alkyl, cycloalkyl, heteroalkyl, —COR$^7$ (wherein R$^7$ is hydrogen or alkyl), or phenyl optionally substituted with one or two substituents independently selected from the group consisting of hydrogen, alkyl, haloalkyl, alkylthio, hydroxy, alkoxy, cyano, nitro, amino, acylamino, monoalkylamino, and dialkylamino;
    $R^4$ and $R^5$ independently represent hydrogen, alkyl, halo, haloalkyl, alkylthio, hydroxy, alkoxy, cyano, nitro, amino, acylamino, monoalkylamino, or dialkylamino;
    $R^6$ is heteroalkyl, heterocyclyl, heterocyclylalkyl, heteroalkylsubstituted heterocyclyl, heteroalkylsubstituted cycloalkyl, heterosubstituted cycloalkyl, —OR$^8$, —S(O)$_n$R$^8$ (wherein n is 0 to 2; and R$^8$ is heteroalkyl, heteroaralkyl, heterocyclyl, or heterocyclylalkyl), —NR$^9$R$^{10}$ (wherein R$^9$ is hydrogen or alkyl and R$^{10}$ is heteroalkyl, heteroaralkyl, heterosubstituted cycloalkyl, heterocyclyl, or heterocyclylalkyl), or —X-(alkylene)-Y-Z (wherein X is a covalent bond, —O—, —NH—, or —S(O)$_{n1}$— where n1 is 0 to 2, and Y is —O—, —NH—, or —S—, and Z is heteroalkyl or SiR$^{11}$R$^{12}$R$^{13}$ where R$^{11}$, R$^{12}$ and R$^{13}$ are independently hydrogen or alkyl), or R$^6$ together with R$^4$ forms a methylenedioxy or ethylenedioxy group when they are adjacent to each other;
or a pharmaceutically acceptable salt thereof.

2. A method of treating a bone fracture in a mammal comprising:
    administering to a mammal having a bone fracture an effective amount of a GSK-3β inhibitor of formula X

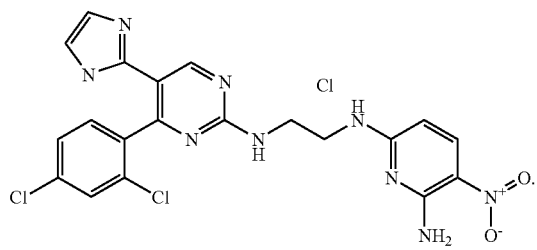

3. A method of treating osteoporosis in a mammal comprising:
    administering to mammal having osteoporosis an effective amount of a GSK-3β inhibitor of Formula (I)

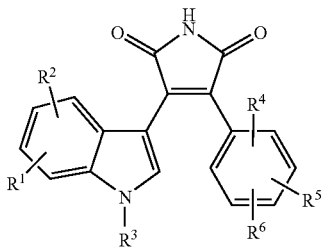

wherein:
    $R^1$ and $R^2$ independently represent hydrogen, alkyl, halo, haloalkyl, alkylthio, hydroxy, alkoxy, cyano, nitro, amino, acylamino, monoalkylamino, or dialkylamino;

R³ represents hydrogen, alkyl, cycloalkyl, heteroalkyl, —COR⁷ (wherein R⁷ is hydrogen or alkyl), or phenyl optionally substituted with one or two substituents independently selected from the group consisting of hydrogen, alkyl, haloalkyl, alkylthio, hydroxy, alkoxy, cyano, nitro, amino, acylamino, monoalkylamino, and dialkylamino;

R⁴ and R⁵ independently represent hydrogen, alkyl, halo, haloalkyl, alkylthio, hydroxy, alkoxy, cyano, nitro, amino, acylamino, monoalkylamino, or dialkylamino;

R⁶ is heteroalkyl, heterocyclyl, heterocyclylalkyl, heteroalkylsubstituted heterocyclyl, heteroalkylsubstituted cycloalkyl, hetereosubstituted cycloalkyl, —OR⁸, —S(O)ₙR⁸ (wherein n is 0 to 2; and R⁸ is heteroalkyl, heteroaralkyl, heterocyclyl, or heterocyclylalkyl), —NR⁹R¹⁰ (wherein R⁹ is hydrogen or alkyl and R¹⁰ is heteroalkyl, heteroaralkyl. heterosubstituted cycloalkyl, heterocyclyl, or heterocyclylalkyl), or —X-(alkylene)-Y-Z (wherein X is a covalent bond, —O—, —NHII-, or —S(O)ₙ₁— where n1 is 0 to 2, and Y is —O—, —NH—, or —S—, and Z is heteroalkyl or SiR¹¹R¹²R¹³ where R¹¹, R¹² and R¹³ are independently hydrogen or alkyl), or R⁶ together with R⁴ forms a methylenedioxy or ethylenedioxy group when they are adjacent to each other;

or a pharmaceutically acceptable salt thereof.

4. A method of treating osteoporosis in a mammal comprising:
administering to a mammal having osteoporosis an effective amount of a GSK-3β inhibitor of formula X

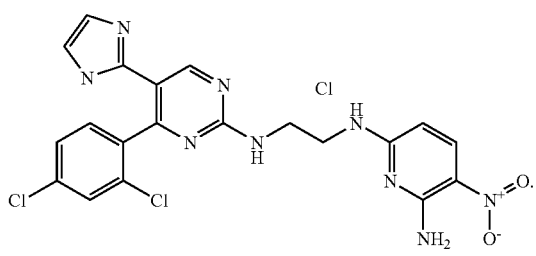

5. The methods of any of claims 1-4 wherein the mammal is a human.

6. The method of claim 5, wherein the human is a female.

7. The method or any of claims 3-4, further comprising administering an antiresorptive agent.

8. The method of claim 1, wherein the compound of Formula (I) is

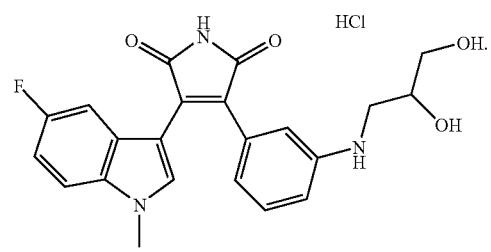

9. The method of any of claims 1-4, wherein the GSK-3β inhibitor is:

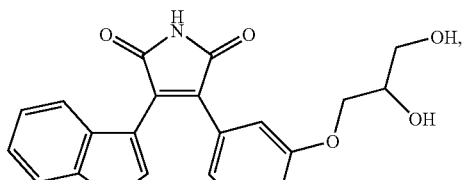

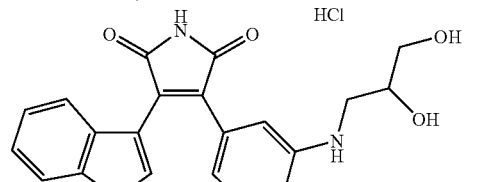

or

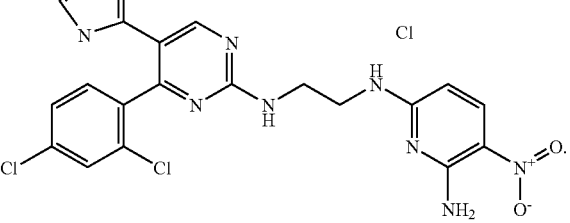

10. The method of any of claims 1-4, wherein the GSK-3β inhibitor is delivered orally.

11. The method of claim 10, wherein treatment with the GSK-3β inhibitor is followed by treatment with an antiresorptive agent.

* * * * *